US009217738B2

(12) United States Patent  
Almond et al.

(10) Patent No.: US 9,217,738 B2  
(45) Date of Patent: Dec. 22, 2015

(54) METHOD FOR CHARACTERIZATION OF THE REDOX CONDITION OF CEMENTITIOUS MATERIALS

(71) Applicant: Savannah River Nuclear Solutions, LLC, Aiken, SC (US)

(72) Inventors: Philip M. Almond, Martinez, GA (US); Christine A. Langton, Aiken, SC (US); David B. Stefanko, North Augusta, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 211 days.

(21) Appl. No.: 13/973,485

(22) Filed: Aug. 22, 2013

(65) Prior Publication Data

US 2015/0056714 A1   Feb. 26, 2015

(51) Int. Cl.
| | | |
|---|---|---|
| *G01N 21/00* | (2006.01) | |
| *G01N 33/38* | (2006.01) | |
| *G01N 31/22* | (2006.01) | |
| *G01N 21/31* | (2006.01) | |

(52) U.S. Cl.
CPC .............. *G01N 33/383* (2013.01); *G01N 31/22* (2013.01); *G01N 21/31* (2013.01)

(58) Field of Classification Search
None
See application file for complete search history.

(56) References Cited

U.S. PATENT DOCUMENTS 6,797,171 B2   9/2004   Bartlett

FOREIGN PATENT DOCUMENTS

WO   WO 85/00044   1/1985

OTHER PUBLICATIONS

Dusing, D. C., et a. Effect of Redox Potential on Leaching from Stabilized/Solidified Waste Materials, 1992, J. Air Waste Manage. Assoc., vol. 42, pp. 56-62.*
Idaho National Laboratory, Appendix Q : Ex Situ Grouting of Pad A Nitrate Salt Tests, 2005, retreived from internet: https://ar.inl.gov/images/pdf/200512/20051206000631JMO.pdf.*
Harbour, J.R. et a. Effects of Temperature and CSSX Organics on Saltstone Processing Properties, 2006, WSRC-TR-2006-00075, retreived from internet: http://sti.srs.gov/fulltext/2006/TR200675.pdf.*
Savannah River Nuclear Solutions, LLC; EP Patent Application No. 14181775.9-1554; Extended European Search Report dated Dec. 18, 2014.
Mary W. Barnes et al.: "Leaching of Saltsone" MRS Proceedings, vol. 44, Jan. 1, 1984 9 pages.
C.A. Langton: "Slag-Based Saltstone Formulations", MRS Proceedings, vol. 112, Jan. 1, 1987 10 pages.
Almond, et al. "Method Evaluation and Field Sample Measurements for the Rate of Movement of the Oxidation Front in Saltstone"; Department of Energy; Aug. 2012.

(Continued)

*Primary Examiner* — Robert Xu
(74) *Attorney, Agent, or Firm* — Dority & Manning, P.A.

(57) ABSTRACT

Disclosed are methods for determining the redox condition of cementitious materials. The methods are leaching methods that utilize an in situ redox indicator that is present in the cementitious materials as formed. The in situ redox indicator leaches from cementitious material and, when the leaching process is carried out under anaerobic conditions can be utilized to determine the redox condition of the material. The in situ redox indicator can exhibit distinct characteristics in the leachate depending upon the redox condition of the indicator.

21 Claims, 1 Drawing Sheet

(56) References Cited

OTHER PUBLICATIONS

Fuentes et al. "The Usefulness of UV-visible and Fluorescence Spectroscopies to Study the Chemical Nature of Humic Substances from Soils and Composts"; *Organic Geochemistry*; 37.12 (2006) pp. 1949-1959.

Rügge et al. "Characterization of Predominant Reductants in an Anaerobic Leachate-Contaminated Aquifer by Nitroaromatic Probe Compounds" *Environmental Science and Technology* 32.1 (1998) pp. 23-31.

Scott et al. "Landfill Management, Leachate Generation, and Leach Testing of Solid Wastes in Australia and Overseas".

Citation of Related Applications.

European Patent Appln. No. 14181844.3-1554; Extended European Search Report; dated Jan. 28, 2015.

Almond, et al. "Cementitious Barriers Parnership Effect of Oxidation on Chromium Leaching and Redox Capacity of Slag-Containing Waste Forms"; Mar. 1, 2013, URL:http://sti.srs.gov/fulltext/CBP-TR-2013-02.pdf.

* cited by examiner

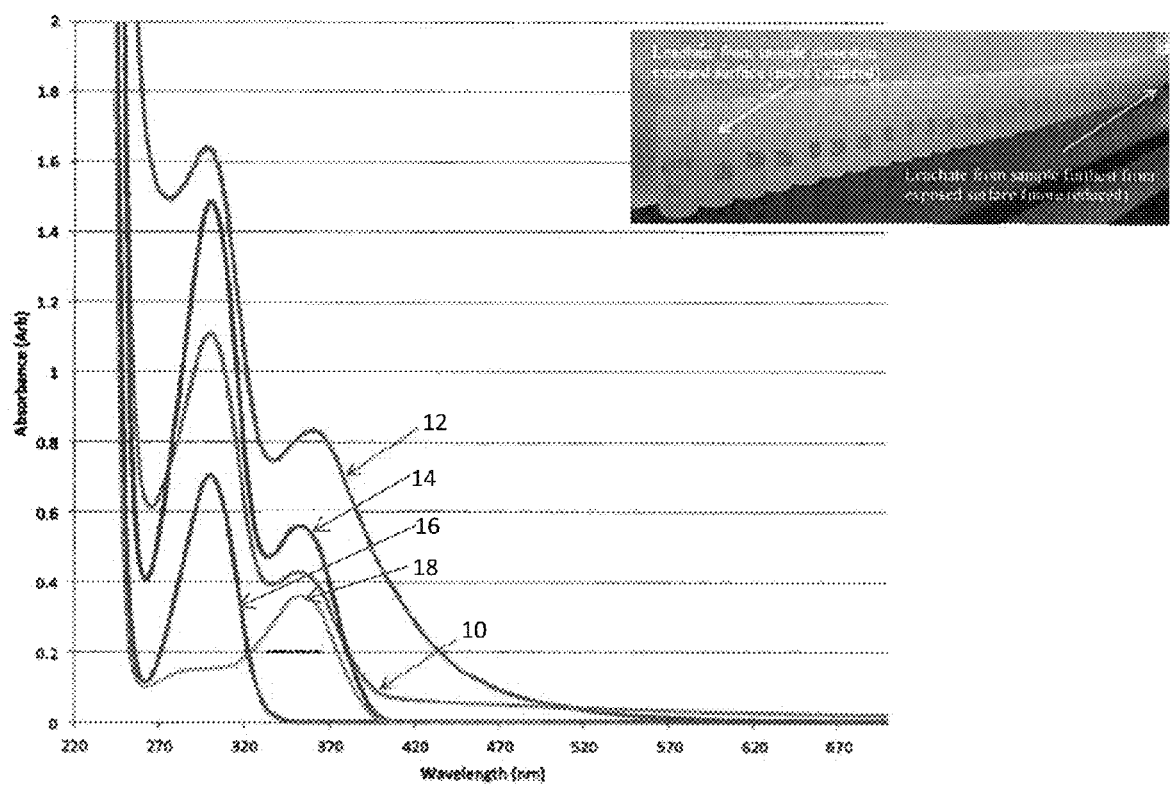

METHOD FOR CHARACTERIZATION OF THE REDOX CONDITION OF CEMENTITIOUS MATERIALS

STATEMENT AS TO RIGHTS TO INVENTIONS MADE UNDER FEDERALLY SPONSORED RESEARCH

This invention was made with Government support under Contract No. DE-AC09-08SR22470 awarded by the United States Department of Energy. The Government has certain rights in the invention.

BACKGROUND

Reprocessing is commonly used to recover plutonium, uranium, and other useful materials from spent nuclear fuel. The current standard method for reprocessing is the PUREX method, which is a liquid-liquid extraction method that can extract both uranium and plutonium independently of each other and from other fission products. Reprocessing methods generate liquid waste that includes both high activity waste (also referred to a high level waste), which carries many of the fission products and transuranic elements generated in the core, and low activity waste (also referred to a low level waste), which carries low activity fission products, actinides, and a plurality of different salts. The low activity waste is further treated to remove actinides and fission products to produce a decontaminated salt solution that, while exhibiting low activity levels, must be properly treated and stored to prevent release of contaminants.

Treatment of the decontaminated salt solution includes mixing it with a blend of cementitious materials to form a grout mixture. Upon curing of the grout mixture through hydration reactions a hardened monolithic cementitious waste form known as saltstone is formed. This particular treatment process is carried out at the Savannah River Site nuclear reservation in South Carolina, USA.

Some contaminants contained in such waste forms (e.g. technetium in saltstone) exhibit a variable solubility depending upon their oxidation state, with the reduced form of the contaminants showing lower solubility. As such, reducing conditions are created in the waste form to slow and/or prevent release of contaminants. For instance, blast furnace slag is utilized in combination with a calcium silicate-based cement (e.g., Portland cement) in forming the saltstone waste form. Blast furnace slag significantly lowers the Eh, or redox potential, relative to traditional cements and thus serves to increase reducing conditions of the saltstone.

Desirably, the reduction capacity of the saltstone will persist over an extended performance period (e.g., 10,000 years) with rates of contaminant release dominated by slow changes in physiochemical properties. Even so, over time the chemical properties of the saltstone will vary as groundwater and dissolved oxygen result in decreasing pH and increasing Eh potential, or oxidation. For example, the rate of oxidation of the cement-slag based waste form saltstone has been calculated to be less than 0.5 millimeters per year based on oxygen diffusion models where diffusion rates change as a function of the square root of time. Models have considered liquid phase transport and a diffusion dominated process independent of flow through a fractured network and a shrinking core model.

Unfortunately, models are theoretical in nature and require experimental data for verification. What are needed in the art are testing methods that can determine the presence of oxidized and reduced zones in cement-slag based waste forms such as saltstone to determine the rate of oxidation of the saltstone and monitor the movement of an oxidation front through the material. The ability to quickly and easily determine the rate of oxidation of cured cementitious materials would be of great use to verify modeling assumptions for long-term use of materials such as saltstone, e.g., for storage as well as to provide a basis for potential processing changes, such as clean cap installation criteria based on maximum allowable saltstone atmospheric exposure time.

SUMMARY

Aspects and advantages of the invention will be set forth in part in the following description, or may be obvious from the description, or may be learned through practice of the invention.

In one embodiment, disclosed is a method for determining the redox condition of a cured cementitious material that includes ground granulated blast furnace slag. The method includes combining a sample of the cementitious material with de-aerated water to form a mixture. The mixture includes a liquid portion, which includes the de-aerated water, and a solid portion. The method also includes maintaining the mixture under anaerobic conditions for a period of time to form a leachate. Following this period of time, the method includes examining the leachate to determine the redox condition of a redox indicator in the leachate. The redox indicator of the leachate is an in situ compound of the cementitious material that leaches from the solid portion to the liquid portion during the contact period. The redox condition of the indicator is indicative of the redox condition of the cementitious material.

These and other features, aspects and advantages of the present disclosure will become better understood with reference to the following description and appended claims.

BRIEF DESCRIPTION OF THE FIGURES

A full and enabling disclosure of the present invention, including the best mode thereof, directed to one of ordinary skill in the art, is set forth in the specification, which makes reference to the appended FIGURE, in which:

FIG. 1 illustrates the spectroscopy results of several leachates obtained from saltstone samples formed with a simulated low level waste liquid.

DETAILED DESCRIPTION

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to methods for determining the redox condition of cementitious materials. More specifically, disclosed methods are relatively simple, fast, and inexpensive leaching methods that can be utilized to determine the oxidation rate and the location of an oxidation front in a cementitious material that includes ground granulated blast furnace slag. The disclosed methods beneficially take advantage of the discovery that cementitious materials can include an in situ redox indicator that leaches from the materials and, when the leaching process is carried out under anaerobic conditions can be utilized to determine the redox condition of the material. As the redox indicator is an in situ indicator, i.e., existing in the as-formed cementitious material and originating from the ground granulated blast furnace slag of the cementitious material, the method does not require the addition of other chemicals to serve as a redox indicator. For instance, no additional redox indicator needs to be added to either the cementitious material during formation or to the sample during testing. During the leaching process, the in situ redox indicator can leach from the solid cementitious sample and into the leachate as a solute. Under the anaerobic conditions of the leaching process, the in situ redox indicator can maintain the redox condition that the indicator had while in the solid sample prior to leaching. Moreover, the in situ redox indicator can exhibit a visibly distinct color in the leachate depending upon the redox condition of the indicator. Thus, the redox condition of the in situ indicator in the anaerobic leachate, and hence the redox condition of the sample, can be easily determined, for instance by visualization and/or spectroscopic examination of the anaerobic leachate.

The location of an oxidation front can be determined by carrying out the process with several samples taken at various locations throughout the cementitious material. The rate of oxidation of the cementitious material can likewise be determined by use of the method.

As utilized herein, the term blend of cementitious material refers to a composite that can be cured via hydration of one or more components of the blend. The blend of cementitious materials can include ground granulated blast furnace slag, generally in conjunction with one or more typical cementitious components.

Ground granulated blast furnace slag (also referred to throughout this disclosure as blast furnace slag) is formed from the slag by-product of cast iron production. The slag by-product is primarily a non-crystalline glassy solid that contains lime, silica and other oxides such as MgO, and $Al_2O_3$, which separate from the metal at temperatures exceeding 1900° C. The ground granulated blast furnace slag is obtained by quenching molten slag in, e.g., water or steam. When the slag is suddenly cooled in the quench, it forms a vitreous granulate. Following the quench, the glass product is then dried and ground to form the ground granulated blast furnace slag.

The specific composition of the blast furnace slag is not particularly limited and can vary depending upon the chemical composition of the slag, as is known in the art. By way of example, the quenched blast furnace slag non-crystalline solid (glass) can include from about 30% by weight to about 50% by weight calcium oxide, from about 25% by weight to about 40% by weight silicon dioxide, from about 5% by weight to about 25% by weight aluminum oxide, and from about 1% by weight to about 20% by weight magnesium oxide, and may include trace amounts (e.g., less than about 3% by weight) of iron oxide and/or sulfur trioxide.

The blast furnace slag can be any grade according to ASTM C989 as is known in the art. For example, the blast furnace slag can be Grade 80, Grade 100, or Grade 120 blast furnace slag, or mixtures thereof.

Blast furnace slag provides multiple benefits to the cementitious material. For instance, it can decrease the pH of an aqueous cementitious mixture, for instance to about pH 11, which can increase the precipitation of heavy metals in the mixture. Blast furnace slag also reduces the solubility of certain radionuclides, which can be of great benefit when utilizing the cementitious materials for long term storage of low level wastes. This can also reduce corrosion of containers that may be used to store the cured materials. The blast furnace slag in the cementitious material can also lead to the precipitation of some cations as sulfides rather than hydroxides, which can further decrease their solubility. Moreover, blast furnace slag in the cementitious material can reduce the permeability of the cured product, which can slow degradation of the cured material and release of materials contained in the cured material.

The blend of cementitious materials can include about 20% or more by weight of the blast furnace slag, for instance from about 40% by weight to 100% by weight, from about 50% by weight to about 98% by weight, or from about 55% by weight to about 95% by weight. In one embodiment, the blend of cementitious materials can include greater than about 50% by weight blast furnace slag.

The low redox potential of the cementitious material mitigates oxidation of the material and associated increased solubility of components of the cured cementitious materials.

While not a requirement, the blend of hydraulic cementitious materials can generally include other materials that can cure via hydration reaction such as, without limitation, calcium silicate based cements and natural and/or synthetic silica or alumino-silica pozzalanic materials. Calcium silicate based cements can include hydraulic cements (i.e., those that cure via hydration) such as Portland cement or Portland blended cements as are generally known in the art. A calcium silicate cement can optionally include additional materials as are known in the art such as gypsum, limestone, hydrated lime, sulfoaluminate, etc.

In one embodiment, the blend of hydraulic cementitious materials can include about 80% or less of a calcium silicate cement. For instance, the cementitious materials can include from about 2% by weight to about 50% by weight, or from about 5% by weight to about 40% by weight calcium silicate cement.

Pozzolanic materials that may be included in the blend of cementitious materials can include siliceous or siliceous and aluminous materials that when in a finely divided state and in the presence of moisture can react with calcium hydroxide to form cementitious compounds. Synthetic pozzolanic materials as may be incorporated in the blend of cementitious materials can be formed, for instance by thermal activation of kaolin-clays to obtain metakaolin, or can be obtained as waste or by-products from high-temperature processes. For instance fly ash as may be obtained as a by-product from coal-fired electricity production can be incorporated in the blend. Silica fume, a by-product of silicon smelting, is another example of a synthetic pozzolanic material as may be incorporated in the blend. Burned organic matter residues rich in silica such as rice husk ash can also be used as pozzolans. Other synthetic pozzolanic materials can include, without limitation, fumed silica, calcined clays, crushed glass (e.g., recycled glass), or materials that contain crushed glass, slags, and the like.

Natural pozzolanic materials that can be included in the blend of cementitious materials can include natural materials of volcanic origin such as volcanic ashes, perlite and pumices. Volcanic materials are generally largely composed of volcanic glass. Other natural pozzolanic materials include deposits in which he volcanic glass has been altered to zeolites by interaction with alkaline waters. Diatomaceous earths, formed by the accumulation of siliceous diatom microskeletons, and other types of finely ground naturally siliceous materials can also be utilized.

When included, the blend of cementitious materials can generally incorporate about 80% or less by weight of one or more pozzolanic materials, for instance from about 20% by weight to about 80% by weight, from about 25% by weight to about 75% by weight, or from about 30% by weight to about 60% by weight.

The blend of cementitious materials can include additional materials as are generally known in the art such as, for instance, and without limitation filler, aggregates, and other structural materials as well as various chemical admixtures that can be utilized to modify characteristics of the cementitious materials.

Aggregates can include fine aggregate, such as natural or manufactured quartz or basaltic sand, and/or course aggregate, such as limestone, granite, gneiss, basalt; heavy weight sand and gravel, e.g., hematite, magnetite or barite or light weight aggregate such as, pumice, vermiculite, or diatomaceous earth. Manufactured aggregates include polymeric beads, formed or crushed ceramic, heavy weight steel or other metal, and light weight expanded clays or shales.

Additives to the cementitious material can include structural fillers such as fibers, e.g., steel, glass, ceramic, carbon, polymeric, or natural fibers, as well as mesh, rebar, and the like. For example, polymeric fibers including polyolefins, polyamides (e.g., nylon), polyester, polymethylpentene, polyacrylonitrile, polyacrylamide, viscose, nylon, PVC, PVA, rayon, or any mixtures thereof. Reinforcing fibers may include but are not limited to various forms of cellulose fibers such as chemical, mechanical or thermal-mechanical pulps, and mineral wool. Fibrous reinforcement materials can include fibers of any suitable size and geometry.

The cementitious material can include additives such as ion exchange resins, zeolites, iron powders, titanate compounds, phosphate compounds, attapulgite clay, and so forth. The additives can be treated as desired, for instance, attapulgite clay may be heat treated (calcined) to modify the surface crystal structure and provide improved adsorptive capabilities to the additive. In one embodiment, the cementitious material can be made less permeable to water by the addition of a clay such as bentonite.

Additives such as air entraining agents, water reducers, plasticizers, water proofing and others can be incorporated in the material. Additives may include but are not limited to density modifiers, dispersing agents, silica fume, geothermal silica, fire retardants, thickeners, pigments, colorants, dispersants, foaming agents, flocculating agents, waterproofing agents, organic density modifiers, aluminum powder, kaolin, alumina trihydrate, mica, calcium carbonate, wollastonite, polymeric resin emulsions, and mixtures thereof. Additive may include organic and/or inorganic molecules, and may comprise small molecules, polymers or mixtures thereof. Additives can include an accelerator for reducing set time, a retarder for delaying set time, a superplasticizer, an air-entraining agent for freeze-thaw resistance, a corrosion inhibitor, an expansive admixture for minimizing shrinkage, a shrinkage reducing admixture, a water repelling admixture, a water reducer (including high-range water reducers), an alkali-aggregate reaction inhibitor (e.g. lithium-based salts), or a mixture thereof.

In one embodiment, the cementitious material can include low activity waste to produce a waste form. According to this embodiment, a radioactive salt solution is combined with a blend of cementitious materials and cured to form the waste material known as saltstone. To form the low activity salt solution used in forming saltstone, a precipitation-adsorption process is first carried out to decontaminate a salt solution including multiple isotopes such as cesium-137, strontium-90, ruthenium-106, plutonium and technetium-99 (Tc-99). One suitable decontamination process is disclosed in U.S. Pat. No. 4,432,893 to Lee, et al., the contents of which are incorporated herein by reference. According to this process, the major radioactive components of the salt solution, cesium-137, strontium-90 and plutonium, are removed by contacting the radioactive waste solution simultaneously with sufficient sodium tetraphenylborate to precipitate the cesium, and with sufficient sodium titanate to adsorb the strontium and plutonium. The solids can then be separated (for example, by cross-flow filtration) from the salt solution. The resulting decontaminated salt solution includes Tc-99, which remains as the predominant long-lived radionuclide. According to one embodiment, such a decontaminated salt solution can be combined with a blend of cementitious materials to form an aqueous-based cementitious slurry, which cures via hydration reactions to produce the waste form referred to as saltstone.

According to the present disclosure, a sample of the cured cementitious material that includes the ground granulated blast furnace slag can be tested to determine the oxidation condition of the waste form. Initially, a sample of the material can be obtained as a core or grab sample from the production/processing/disposal facility or from a sample produced in the laboratory. The sample can be tested as obtained or, in one embodiment, the sample can be crushed or ground to increase the surface area of the sample. When the sample is ground, the particulate size of the sample is not particularly critical.

In one embodiment, a bore or grab sample can be sliced into "depth discrete" wafers and each wafer tested to determine the oxidation profile, and depth to which the sample has been oxidized. In one embodiment, the sample can be obtained and (optionally) crushed to smaller size in an anaerobic atmosphere. While this is not a requirement of the testing methods, in those embodiments in which the sample is not obtained and treated in an anaerobic atmosphere, the sample should be tested as quickly as possible following initial separation from the bulk material, so as to avoid oxidation of reduced components of the test sample during sample preparation.

To determine the redox condition of the cementitious material, the sample is combined with anaerobic water and held in an anaerobic atmosphere for a period of time to promote leaching of the in situ redox indicator from the sample and at the same time prevent inadvertent oxidation of the redox indicator during the leaching process. The testing water can be de-aerated according to any suitable method. For instance, in one embodiment the water can be boiled for a period of approximately 15 minutes and cooled in a sealed container. In one embodiment, the anaerobic water can be ASTM Type 1 water and meet the requirements for deionized water as described in ASTM 1193. For instance, the water can have a resistivity at 25° C. of less than about 18 MΩ-cm and can have a conductivity at 25° C. of less than about 0.056 µS/cm.

The mixture can be agitated to encourage contact between the solid and liquid. For instance, the mixture can be stirred, rotated, tumbled, etc. The contact/leaching/extraction time is variable. Results have been obtained for samples leached 18 hr and 28 days. Longer and shorter leaching times are viable/reasonable and depend on the properties of the waste form.

To encourage extraction of the redox indicator from the hydrated cementitious material in the leaching solution, the mixture including the solid sample and the anaerobic water can be held in an anaerobic atmosphere for a period of time of about 10 minutes or more, for instance from about 15 minutes to about 24 hours, to allow leaching of materials from the solid to the leachate. The preferred time for the leaching process can vary depending upon the size of the sample, the particulate size of the sample, etc. as is known in the art.

Following a period of time, the leachate can be examined to determine the redox condition of the in situ redox indicator. Without wishing to be bound to any particular theory, it is believed that the in situ redox indicator is a component of the ground granulated blast furnace slag. Under the anaerobic conditions of the test, in those situations in which the cementitious sample is still in a reduced state, the in situ redox indicator will be in a preserved or reduced state, and will have a yellow color. When the cementitious sample is oxidized, the in situ redox indicator will be oxidized or decomposed, and the leachate will appear colorless. Thus, in one embodiment, the leachate can be examined visually to determine the redox condition of the sample, In one embodiment, the leachate can be examined via spectroscopy to determine the redox condition of the sample. The leachate from a reduced sample has a characteristic absorption profile as compared to the leachate from an oxidized sample. The absorption profile of the reduced leachate includes absorption bands at $\lambda_{max}$=298 nm and 359 nm and can have a broad absorption band reaching to about 500 nm. The leachate from an oxidized sample, in contrast, exhibits reduced absorption in those regions. In an oxidized sample, $\lambda_{max}$=301 nm and 352 nm.

One or more samples can be taken from a bulk cementitious material to determine the oxidation condition of the material. For instance, multiple samples can be taken at various depths as determined from a surface of the material to determine the location of an oxidation front within the sample. The location of an oxidation front can be determined, for instance by incremental sample testing of a bore taken through the depth of the material, and the rate of oxidation of the material can be determined. In one embodiment, a single sample can be taken at the farthest depth from an exposed surface of the cementitious material to determine if the entire sample is oxidized.

The present disclosure may be better understood with reference to the example, set forth below.

EXAMPLE 1

A low level waste simulant was formed including the components of the table, below:

| Compound | Molarity (moles/liter) | Molecular Mass (grams/mole) | Amount/Liter (grams) |
|---|---|---|---|
| Al(NO$_3$)·9H$_2$O | 0.110 | 375.129 | 41.23 |
| 50 wt. % NaOH | 1.551 | 39.998 | 124.07 |
| Na$_2$SO$_4$ | 0.059 | 142.042 | 8.32 |
| Na$_2$CO$_3$ | 0.148 | 105.990 | 15.64 |
| Na$_2$NO$_3$ | 2.116 | 84.995 | 179.86 |
| NaNO$_2$ | 0.336 | 68.996 | 23.20 |

The simulant was mixed with a blend of cementitious materials including:
  45 wt. % ground granulated blast furnace slag
  45 wt. % thermally beneficiated Class F fly ash
  10 wt. % ordinary Portland cement
The blend of cementitious materials was at a nominal 0.6 water to blend ratio.

Samples were prepared by first adding the simulant solution to a beaker. The simulant solution was stirred by a mechanical mixer containing a 6-blade paddle impeller at about 250 rpm. The components of the blend were blended in a bag and then added to the simulant as the simulant was stirred. The resultant grout slurry was mixed for about three minutes at an increased rpm that produces a vortex in the grout without entraining air. The grout was subsequently poured into 1½"×3¹¹⁄₁₆" polypropylene sample cylinders and cured with an open top in air to create an oxidation front such that the cured cylinders included an oxidized portion and a reduced portion. The samples were cured in a humid chamber at ambient temperature and 65-70% relative humidity.

For testing, cylinders were removed from the plastic vials and wafers were sliced from the cylinders starting from the top surface that was exposed to air. A Techcut4™ saw with a low concentration diamond blade and jig was used to cut the wafers.

Wafer samples were ground using a mortar and pestle.

ASTM Type 1 water (ASTM 1193) was utilized as the leaching solution. The pH of the water was 6.94. The water was de-aerated by boiling in an open stainless steel container for 15 minutes. The water was subsequently cooled to room temperature in a sealed container that was placed in an ice bath before contacting the crushed samples. Less than 5 hours elapsed between boiling the water and filling the leaching vials.

A zero-head space leaching vessel was utilized. A crushed sample was placed in a leaching vial and the vial was completely filled with the de-aerated water. Care was taken to minimize the sample handling time and thereby the time the demolded samples were exposed to oxygen. Minimal oxidation during sample preparation was later confirmed by the reduced state of the samples taken from greater depths of the cylinders.

Vials were filled so that no air pocket remained after capping. Multiple vials were individually wrapped and placed inside a large mouth bottle that was tumbled end-over-end for 20 hours. The tumbler rotated at 30 rpm.

After tumbling, the leachates were extracted and filtered using a 0.45 micron membrane. The leachate samples were analyzed visually and also in a 1 cm square quartz cuvette using a Hach™ DR 5000 spectrophotometer that scanned from 900 to 200 nm at 1 nm steps.

It was found that the anaerobic leachate from the reduced samples was pale yellow in color while the leachate from the oxidized samples was colorless to the eye. It was observed that exposure of the yellow leachate to air corresponded with the leachate changing form yellow to colorless.

FIG. 1 illustrates the UV-Vis absorbance results of a leachate from the air-exposed sample at the surface of a cured cylinder 10 and of a leachate from a sample taken farthest from the air-exposed surface of the same cured cylinder 12. FIG. 1 also presents the results for the simulant alone 14, NaNO$_3$ 16, and NaNO$_2$ 18. The deepest sample leachate 12 appeared yellow and the sample from the air-exposed surface 10 appeared colorless. As can be seen the reduced sample 12 provides a unique absorbance spectrum as compared to the oxidized sample 10.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for determining the redox condition of a cured cementitious material, the method comprising:
combining a sample of a cementitious material with de-aerated water to form a mixture, wherein the cementitious material includes ground granulated blast furnace slag, wherein the cementitious material includes about 20% or more by weight of the ground granulated blast furnace slag, the mixture including a liquid portion that includes the de-aerated water and a solid portion;
maintaining the mixture under anaerobic conditions for a period of time of about 10 minutes or more to form a leachate;
examining the leachate visually and/or by use of spectroscopy following the period of time to determine the color of the leachate, the color of the leachate being indicative of the redox condition of the cured cementitious material.

2. The method according to claim 1, wherein the cementitious material includes a calcium silicate cement.

3. The method according to claim 2, wherein the calcium silicate cement comprises Portland cement.

4. The method according to claim 2, wherein the cementitious material includes about 80% by weight or less of the calcium silicate cement.

5. The method according to claim 1, wherein the cementitious material includes a natural or synthetic silica or alumino-silica pozzalanic material.

6. The method according to claim 5, wherein the pozzolanic material comprises fly ash.

7. The method according to claim 5, wherein the cementitious material includes about 80% by weight or less of the pozzolanic material.

8. The method according to claim 1, wherein the cementitious material comprises a filler or an aggregate.

9. The method according to claim 1, wherein the cementitious material comprises a rheology modifying additive.

10. The method according to claim 1, wherein the cementitious material comprises a low activity waste.

11. The method according to claim 1, the method further comprising obtaining the sample from the cementitious material under anaerobic conditions.

12. The method according to claim 1, further comprising treating the sample to increase the surface area of the sample prior to the step of combining the sample with the de-aerated water.

13. The method according to claim 12, wherein the sample is treated under anaerobic conditions.

14. The method according to claim 1, further comprising agitating the sample during the step of maintaining the mixture under anaerobic conditions.

15. The method according to claim 1, the method comprising repeating the method with one or more additional samples obtained from the cementitious material, wherein the one or more additional samples are obtained from different depths of the cementitious material as determined from a surface of the cementitious material.

16. The method according to claim 1, wherein the method is utilized to determine the location of an oxidation front in the cementitious material.

17. The method according to claim 1, wherein the method is utilized to determine the rate of oxidation of the cementitious material.

18. The method according to claim 1, wherein the ground granulated blast furnace slag comprises lime, silica, and one or more other oxides.

19. The method according to claim 18, wherein the ground granulated blast furnace slag comprises from about 30% by weight to about 50% by weight calcium oxide, from about 25% by weight to about 40% by weight silicon dioxide, from about 5% by weight to about 25% by weight aluminum oxide, from about 1% by weight to about 20% by weight magnesium oxide, and trace amounts of iron oxide and/or sulfur trioxide.

20. The method according to claim 1, the ground granulated blast furnace slag comprising iron oxide and sulfur trioxide.

21. The method according to claim 1, the ground granulated blast furnace slag comprising sulfur.

* * * * *